(12) United States Patent
Woo et al.

(10) Patent No.: US 9,974,447 B2
(45) Date of Patent: May 22, 2018

(54) METHOD FOR MEASURING BLOOD PRESSURE, AND APPARATUS FOR MEASURING BLOOD PRESSURE BASED ON SAID METHOD

(71) Applicant: UMEDIX CORPORATION LIMITED, Seongnam Gyeonggi-do (KR)

(72) Inventors: Sung Hun Woo, Suwon (KR); Yun Young Choi, Seoul (KR); Yun Seok Chang, Seoul (KR)

(73) Assignee: UMEDIX CORPORATION LIMITED, Seongnam, Gyeonggi-do (KR)

( * ) Notice: Subject to any disclaimer, the term of this patent is extended or adjusted under 35 U.S.C. 154(b) by 634 days.

(21) Appl. No.: 14/469,658

(22) Filed: Aug. 27, 2014

(65) Prior Publication Data

US 2014/0364747 A1    Dec. 11, 2014

Related U.S. Application Data

(63) Continuation of application No. PCT/KR2012/009676, filed on Nov. 15, 2012.

(30) Foreign Application Priority Data

Mar. 8, 2012 (KR) .................. 10-2012-0023995

(51) Int. Cl.
*A61B 5/02* (2006.01)
*A61B 5/022* (2006.01)
*A61B 5/00* (2006.01)

(52) U.S. Cl.
CPC ............ *A61B 5/022* (2013.01); *A61B 5/7275* (2013.01); *A61B 5/0002* (2013.01); *A61B 2560/0257* (2013.01)

(58) Field of Classification Search
CPC .................. A61B 5/022; A61B 5/7275; A61B 2560/0257; A61B 5/0002
See application file for complete search history.

(56) References Cited

U.S. PATENT DOCUMENTS 2,799,270 A * 7/1957 Rodbard ................ A61B 5/021
                                              600/491
4,023,563 A * 5/1977 Reynolds ............... H03K 5/153
                                              600/485

(Continued)

FOREIGN PATENT DOCUMENTS

JP        08-187227 A        7/1996
JP        2004-105548 A      4/2004

(Continued)

OTHER PUBLICATIONS

Derwent Abstract for the Roline reference above.*
International Search Report for PCT/KR2012/009676 dated Mar. 22, 2013 from Korean Intellectual Property Office.

*Primary Examiner* — Tiffany Weston
*Assistant Examiner* — Tho Tran
(74) *Attorney, Agent, or Firm* — Paralus Law Group, PLLC

(57) ABSTRACT

According to an aspect of the present invention, there is provided a blood pressure measuring apparatus including a pressure sensor unit configured to sense an atmospheric pressure, an applied pressure, and a blood pressure of a blood vessel delivered to a skin and output an electrical signal indicating a result of sensing the pressures, while in contact with the skin; a signal division unit configured to receive the electrical signal and divide the electrical signal into a divided electrical signal which includes a direct current (DC) signal and an alternating current (AC) signal; a signal processor unit configured to process the divided electrical signal; and a blood pressure calculation unit con- (Continued)

figured to calculate the applied pressure using the processed electrical signal and calculate a blood pressure average using the calculated applied pressure and a swing value of the electrical.

13 Claims, 7 Drawing Sheets

(56) References Cited

U.S. PATENT DOCUMENTS

| | | | | |
|---|---|---|---|---|
| 4,271,843 A * | 6/1981 | Flynn | ............... | A61B 5/02225 600/494 |
| 4,958,636 A * | 9/1990 | Blandino | ............... | A61B 5/022 600/301 |
| 5,111,817 A * | 5/1992 | Clark | ............... | A61B 5/02007 356/41 |
| 8,155,758 B2 * | 4/2012 | Roline | ............... | A61N 1/36564 607/119 |
| 8,465,424 B2 * | 6/2013 | Aggarwal | ............ | A61B 5/0002 600/300 |
| 2004/0019285 A1 * | 1/2004 | Eigler | ............... | A61B 5/0215 600/488 |
| 2007/0276265 A1 * | 11/2007 | Borgos | ............... | A61B 5/02225 600/490 |
| 2008/0228089 A1 * | 9/2008 | Cho | ............... | A61B 5/021 600/485 |
| 2012/0108985 A1 * | 5/2012 | Shyu | ............... | A61B 5/02116 600/485 |
| 2012/0238887 A1 * | 9/2012 | Gerdt | ............... | A61B 5/02116 600/499 |

FOREIGN PATENT DOCUMENTS

| | | |
|---|---|---|
| JP | 2004-121616 A | 4/2004 |
| JP | 2007-167171 A | 7/2007 |

* cited by examiner

METHOD FOR MEASURING BLOOD PRESSURE, AND APPARATUS FOR MEASURING BLOOD PRESSURE BASED ON SAID METHOD

CROSS REFERENCE TO PRIOR APPLICATIONS

This application is a Continuation of PCT International Patent Application No. PCT/KR2012/009676 (filed on Nov. 15, 2012) under 35 U.S.C. § 365(C), which claims priority to Korean Patent Application No. 10-2012-0023995 (filed on Mar. 8, 2012), which are all hereby incorporated by reference in their entirety.

TECHNICAL FIELD

The present invention relates to apparatuses and methods of measuring blood pressure.

BACKGROUND ART

With a conventional method and apparatus for measuring blood pressure, it is difficult to directly measure the pressure of blood pumped from the heart. Thus, methods of indirectly measuring blood pressure have been used. A Korotkoff method is a representative method among these methods. In the Korotkoff method, the humeral region of a patient is wound with a band, the band is expanded by injecting air into the band until blood does not flow through blood vessels, and the blood pressure of the patient is measured using sound generated by gradually reducing pressure applied to the band. That is, when pressure is applied to the band by injecting air into the band and the amount of the air is gradually reduced, the sound of the pulse of the artery is heard similar to the sound heard when an object is feebly tapped. In this case, the pressure at this moment is systolic pressure which is blood pressure when the heart contracts. Then, when the amount of the air injected into the band is further reduced, there is a moment that the sound of the pulse increases more and then suddenly vanishes. The blood pressure at this moment is diastolic pressure, i.e., pressure in the blood vessels when the ventricles of the heart contract and expand again.

As another example, the SPO2 method has been also used to measure blood pressure. In the SPO2 method, oxygen saturation in a capillary vessel is measured and the blood pressure of a subject is determined based on the level of hemoglobin in blood flow.

DETAILED DESCRIPTION OF THE INVENTION

Technical problem

The conventional methods described above are, however, accompanied by various problems. First, in the Korotkoff method, blood pressure is measured by pressing down on the humeral region of a subject so that blood may not flow through blood vessels and gradually reducing pressure applied to the humeral region. However, blood cannot be delivered to human tissues while the humeral region is pressurized. Thus, oxygen and nutrients are not supplied to the human tissues and the capillary vessels are thus ruptured, thereby causing terminus tissues to necrotize. Accordingly, it is impractical to perform the Korotkoff method on even normal persons five times or more per day. In particular, serious problems may occur when the Korotkoff method is performed on a diabetic.

Also, in the SPO2 method of measuring oxygen saturation, the level of hemoglobin is not closely related to blood pressure and thus the difference between individuals is large. In particular, in the case of a pregnant woman with a fetus, a hemoglobin level is high but blood pressure is low. Thus, it is not practical to apply the SPO2 method to the pregnant woman. In the case of a diabetic, the viscosity of blood is high and blood pressure of the diabetic is difficult to precisely measure with the SPO2 method. Thus, there is a need to develop an apparatus and method for measuring blood pressure which is useful for persons whose blood pressure need to be continuously monitored.

To solve the above conventional problems, one of the objectives of the present invention is to provide an apparatus and method for continuously measuring and monitoring blood pressure. Another objective of the present invention is to provide an apparatus and method for precisely measure the blood pressure of a particular subject, such as a diabetic, a pregnant woman, etc.

Technical solution

According to an aspect of the present invention, there is provided a blood pressure measuring apparatus including a pressure sensor unit configured to sense an atmospheric pressure, an applied pressure, and a blood pressure of a blood vessel delivered to a skin and output an electrical signal indicating a result of sensing the pressures, while in contact with the skin; a signal division unit configured to receive the electrical signal and divide the electrical signal into a divided electrical signal which includes a direct current (DC) signal and an alternating current (AC) signal; a signal processor unit configured to process the divided electrical signal; and a blood pressure calculation unit configured to calculate the applied pressure using the processed electrical signal and calculate a blood pressure average using the calculated applied pressure and a swing value of the electrical signal.

In one embodiment, the pressure sensor unit may include a housing including a concave structure; and a pressure sensor installed in the housing and configured to sense a pressure in the concave structure.

In one embodiment, the pressure sensor unit may sense the atmospheric pressure and the applied pressure, output a DC signal indicating a result of sensing the atmospheric pressure and the applied pressure, sense the pressure of the blood vessel delivered to the skin, and output an AC signal indicating a result of sensing the delivered pressure.

In one embodiment, the signal processor unit may include an amplifier configured to amplify an input signal; and an analog-to-digital converter (ADC) configured to perform digital conversion on the amplified input signal.

In one embodiment, the signal processor unit may include an amplifier configured to amplify an input signal; a level shifter configured to shift a level of the input signal; and a plurality of analog-to-digital converters (ADCs) configured to perform digital conversions on outputs of the amplifier and the level shifter.

In one embodiment, the signal division unit may include a high-pass filter unit configured to remove a DC signal from an output signal of the pressure sensor unit and output an AC signal.

In one embodiment, the high-pass filter unit may include at least one of a first or higher order high-pass filter and a capacitor.

In one embodiment, the blood pressure calculation unit may include an arithmetic unit configured to calculate a blood pressure average by performing an arithmetic operation on the calculated applied pressure and the swing value of the electrical signal; a memory unit configured to store the applied pressure and the swing value of the electrical signal; an input/output (I/O) unit configured to receive a signal from the signal processor unit and output a value calculated by the arithmetic unit; and a control unit configured to control the arithmetic unit, the memory unit, and the I/O unit.

In one embodiment, the apparatus may further include a display unit configured to display the blood pressures calculated by the blood pressure calculation unit.

In one embodiment, the apparatus may further include a communication unit configured to communicate with at least one of an external server and a terminal through wired/wireless communication to transmit the pressures calculated by the blood pressure calculation unit.

In one embodiment, the blood pressure calculation unit may calculate the swing value from the difference between a maximum value and a minimum value of the electrical signal, and calculate the applied pressure by subtracting the atmospheric pressure from a pressure sensed by and output from the pressure sensor unit.

In one embodiment, the blood pressure calculation unit may calculate a rate of transfer of pressure via subcutaneous tissue, based on the applied pressure.

In one embodiment, the blood pressure calculation unit may calculate the blood pressure average from a slope of a straight line formed by coordinate pairs including the calculated applied pressure and the swing value of the electrical signal.

In one embodiment, the blood pressure calculation unit may calculate a pulse pressure by dividing a value, which is obtained by subtracting a second constant from the product of the blood pressure average and a first constant, by the applied pressure.

According to another aspect of the present invention, there is provided a blood pressure measuring apparatus including a pressure sensor unit configured to sense an atmospheric pressure, an applied pressure, and a blood pressure of a blood vessel delivered to a skin and output an electrical signal indicating a result of sensing the pressures, while in contact with the skin; a signal division unit configured to receive the electrical signal and divide the electrical signal into a divided electrical signal which includes a direct current (DC) signal and an alternating current (AC) signal; a signal processor unit configured to process the divided electrical signal; and a blood pressure calculation unit configured to calculate the applied pressure using the processed electrical signal and calculate a pulse pressure using the calculated applied pressure and a swing value of the electrical signal.

In one embodiment, the pressure sensor unit may include a housing including a concave structure; and a pressure sensor installed in the housing and configured to sense a pressure in the concave structure.

In one embodiment, the pressure sensor unit may sense the atmospheric pressure and the applied pressure, output a DC signal indicating a result of sensing the atmospheric pressure and the applied pressure, sense the pressure of the blood vessel delivered to the skin, and output an AC signal indicating a result of sensing the delivered pressure.

In one embodiment, the signal processor unit may include an amplifier configured to amplify an input signal; and an analog-to-digital converter (ADC) configured to perform digital conversion on the amplified input signal.

In one embodiment, the signal processor unit may include an amplifier configured to amplify an input signal; a level shifter configured to shift a level of the input signal; and a plurality of analog-to-digital converters (ADCs) configured to perform digital conversions on outputs of the amplifier and the level shifter into digital signals.

In one embodiment, the signal division unit may include a high-pass filter unit configured to remove a DC signal from an output signal of the pressure sensor unit and output an AC signal.

In one embodiment, the blood pressure calculation unit may include an arithmetic unit configured to calculate a pulse pressure by performing an arithmetic operation on the calculated applied pressure and the swing value of the electrical signal; a memory unit configured to store the applied pressure and the swing value of the electrical signal; an input/output (I/O) unit configured to receive a signal from the signal processor unit and output a value calculated by the arithmetic unit; and a control unit configured to control the arithmetic unit, the memory unit, and the I/O unit.

In one embodiment, the apparatus may further include a display unit configured to display the calculated pressures.

In one embodiment, the apparatus may further include a communication unit configured to communicate with at least one of an external server and a terminal through wired/wireless communication to transmit the calculated pressures.

In one embodiment, the blood pressure calculation unit may calculate the swing value from the difference between a maximum value and a minimum value of the electrical signal, and calculate the applied pressure by subtracting the atmospheric pressure from a pressure sensed by and output from the pressure sensor unit.

In one embodiment, the blood pressure calculation unit may calculate a rate of transfer of pressure via subcutaneous tissue, based on the applied pressure.

In one embodiment, the blood pressure calculation unit may calculate a blood pressure average from a slope of a segment formed by coordinate pairs of the calculated applied pressure and the swing value of the electrical signal, and calculates the pulse pressure by dividing a value, which is obtained by subtracting a fourth constant from a product of the blood pressure average and a third constant, by the applied pressure and multiplying a division result by the swing value.

According to another aspect of the present invention, there is provided a blood pressure measuring method including sensing an atmospheric pressure, an applied pressure, and a blood pressure of a blood vessel delivered to a skin and outputting an electrical signal indicating a result of sensing the pressures; dividing the electrical signal into a divided electrical signal which includes a direct current (DC) signal and an alternating current (AC) signal; processing the divided electrical signal; calculating the applied pressure using the processed electrical signal; and calculating a blood pressure average using the calculated applied pressure and a swing value of the processed electrical signal.

In one embodiment, the sensing and the outputting include sensing the atmospheric pressure and the applied pressure, outputting a DC signal indicating a result of sensing the atmospheric pressure and the applied pressure, sensing the pressure of the blood vessel delivered to the skin, and outputting an AC signal indicating a result of sensing the delivered pressure.

In one embodiment, the processing of the divided electrical signal may comprise amplifying the divided electrical signal or shifting levels of the divided electrical signal; and performing digital conversions on the amplified or level-shifted electrical signal.

In one embodiment, the method may further include communicating with at least one of an external server and a terminal through wired/wireless communication to transmit the calculated average blood pressure.

In one embodiment, the calculating of the blood pressure average may include calculating the swing value by calculating the difference between a maximum value and a minimum value of the electrical signal; and calculating the applied pressure by subtracting the atmospheric pressure from a pressure sensed by and output from the pressure sensor.

In one embodiment, the calculating of the blood pressure average may include calculating a rate of transfer of pressure via subcutaneous tissue using the applied pressure.

In one embodiment, the calculating of the blood pressure average may include calculating coordinate pairs including the calculated applied pressure and the swing value; and calculating the blood pressure average from a slope of a segment formed by the coordinate pairs.

In one embodiment, after the calculating of the blood pressure average, the method may further include calculating a pulse pressure by dividing a value, which is obtained by subtracting a second constant from the product of the blood pressure average and a first constant, by the applied pressure.

Advantageous Effects

According to one embodiment of the present invention, the blood pressure of a subject can be continuously measured. According to one embodiment of the present invention, the blood pressure of a particular subject, e.g., a diabetic, a pregnant woman, etc., can be precisely measured. According to one embodiment of the present invention, a blood pressure system that is easy to carry and is always wearable is provided.

MODE OF THE INVENTION

Figure 1:
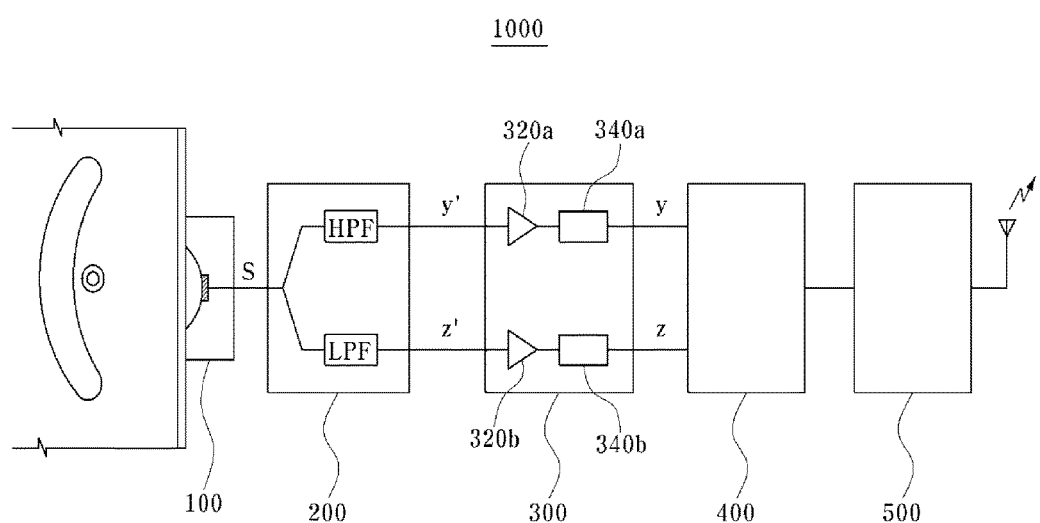
FIG. 1 is a brief block diagram of a blood pressure measuring apparatus according to one embodiment of the present invention.

The following descriptions about the present invention are merely embodiments for describing the present invention in a structural/functional view and the scope of the invention should not be construed as being limited to the embodiments set forth herein. That is, various changes may be made in these exemplary embodiments without departing from the principles and spirit of the invention, the scope of which is defined in the claims and their equivalents.

The terminology used herein should be understood as described below.

It will be understood that, although the terms "first," "second," "third," etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

It will be understood that when an element or layer is referred to as being "on" another element or layer, the element or layer can be directly on another element or layer or intervening elements or layers. In contrast, when an element is referred to as being "in contact with" another element or layer, there are no intervening elements or layers present. Other expressions describing the relationship between elements or layers, such as "via", "directly via", "between," "directly between," "adjacent to," and "directly adjacent to" should be understood likewise.

As used herein, the singular forms "a," "an," and "the" are intended to include the plural forms as well, unless the context clearly indicates otherwise. It will be further understood that the terms "comprise" and/or "include", when used in this specification, specify the presence of stated features, integers, steps, operations, elements, and/or components, but do not preclude the presence or addition of one or more other features, integers, steps, operations, elements, components, and/or groups thereof.

Operations included in a process may be performed differently from the described order unless specified otherwise. That is, the operations may be performed in the described order, performed substantially at the same time, or performed in an order opposite to the described order.

In the drawings referred to describe the embodiments set forth herein, sizes, heights, thicknesses, etc. of layers and regions may be exaggerated for clarity and should not understood as being enlarged or reduced in a certain ratio. Also, in the drawings, some elements may be intentionally reduced and some elements are intentionally enlarged in terms of size, height, or thickness thereof Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A method of measuring blood pressure according to an embodiment of the present invention will now be described with reference to the accompanying drawings. FIGS. 1 to 5 are diagrams illustrating a blood pressure measuring apparatus according to an embodiment of the present invention. FIG. 1 is a brief block diagram of a blood pressure measuring apparatus 1000 according to one embodiment of the present invention. Referring to FIG. 1, the blood pressure measuring apparatus 1000 according to one embodiment of the present invention includes a pressure sensor unit 100, a signal division unit 200, a signal processor unit 300, and a blood pressure calculation unit 400. According to the one embodiment, the blood pressure measuring apparatus 1000 further includes a communication unit 500.

Figure 2:
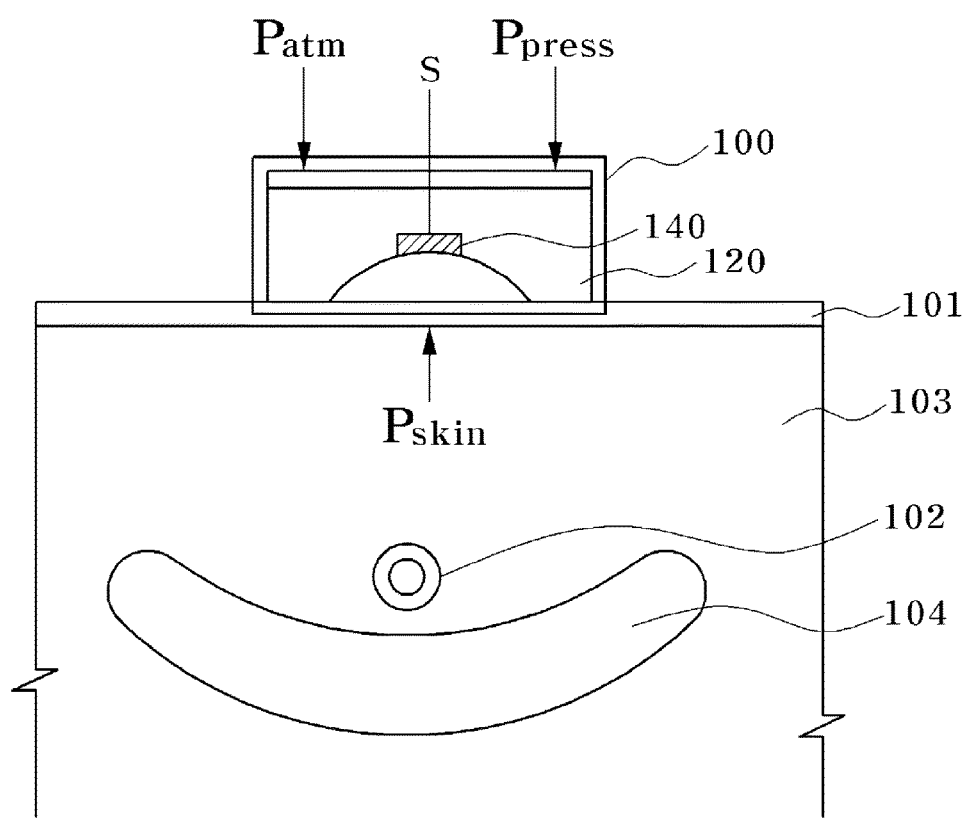
FIG. 2 is a diagram schematically illustrating a pressure sensor.

FIG. 2 is a diagram schematically illustrating the pressure sensor unit 100. Referring to FIGS. 1 and 2, the pressure sensor unit 100 senses atmospheric pressure Patm, applied pressure Ppress, and pressure Pskin of a blood vessel delivered to the skin of a subject and outputs an electrical signal indicating a result of sensing the pressures, in a state in which the pressure sensor unit 100 is in contact with the skin 101 of a subject. In one embodiment, the pressure sensor unit 100 includes a housing 120 having a concave structure, and a pressure sensor 140 which is installed in the housing 120, senses the pressure of air contained between the concave structure of the housing 120 and the skin 101 and the blood pressure in a blood vessel 102 which is delivered to the skin 101, and then outputs an electrical signal indicating a result of sensing the pressure of air and the blood pressure. In one embodiment, the pressure sensor 140 senses atmospheric pressure Patm, the applied pressure Ppress, and pressure Pskin applied to the skin 101 by the blood vessel 102 via a subcutaneous tissue 103. Since in general, the atmospheric pressure Patm has a constant value of 760 mmHg, an electrical signal output from the pressure sensor 140 when the pressure sensor 140 senses the atmospheric pressure Patm has a direct current (DC) component. The pressure Pskin delivered to the skin 101 means the blood pressure in the blood vessel 102 which is applied to the pressure sensor 140 via the blood vessel 102, the subcutaneous tissue 103, and the skin 101. Since the pressure of the blood vessel 102 is periodically switched between a systolic pressure which is a maximum pressure and a diastolic pressure which is a minimum pressure as the heart contracts and relaxes, the pressure Pskin delivered to the skin 101 is also periodically switched between a maximum level and a minimum level. Also, a variation in the form of the pressure Pskin according to time is similar to that in the form of the blood pressure in the blood vessel 102 according to time. Thus, the electrical signal output from the pressure sensor 140 when the pressure sensor 140 senses the pressure Pskin delivered to the skin 101 is in a form of an alternating current (AC) signal that changes according to time. The applied pressure Ppress means a pressure sensed by the pressure sensor 140, such as a pressure when the pressure sensor unit 100 is pressed by a finger of a user or the like or a pressure that increases or decreases when a part of the body of the subject who wears the pressure sensor unit 100 moves, except for the atmospheric pressure Patm and the pressure Pskin of the blood vessel 102 delivered to the skin 101. In the present disclosure, the applied pressure Ppress is a generic term for any applied pressure except for the atmospheric pressure Patm and the pressure Pskin delivered to the skin 101. Thus, an electrical signal output from the pressure sensor 140 when the pressure sensor 140 senses the applied pressure Ppress is in the form of a DC signal that does not change or slightly changes according to time. Thus, a signal output from the pressure sensor unit 100 when the pressure sensor unit 100 senses the atmospheric pressure Patm and the applied pressure Ppress is in the form of a DC signal, and a signal output from the pressure sensor unit 100 when the pressure sensor unit 100 senses the pressure Pskin delivered to the skin 101 is in the form of an AC signal. Accordingly, an overall signal s output from the pressure sensor unit 100 is in the form in which the DC signal and the AC signal overlap each other. Reference numeral "104" that is not described here denotes a bone that may present in subcutaneous tissue.

Figure 3:
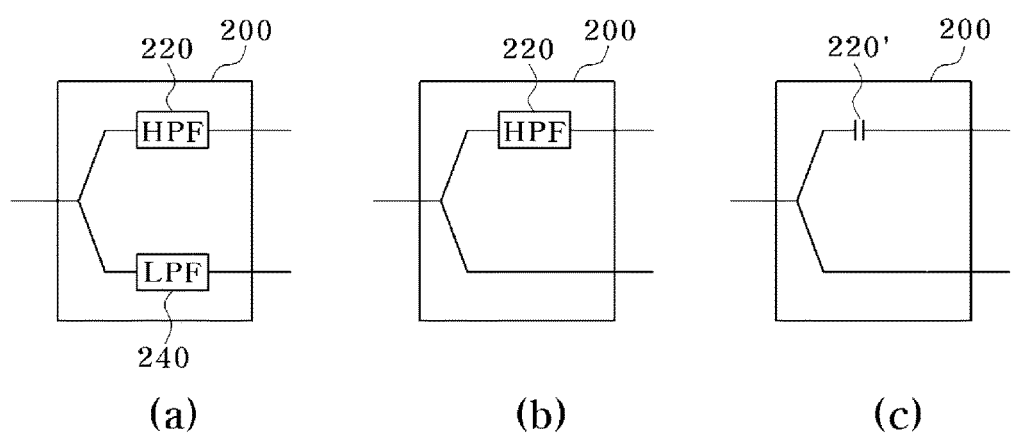
FIG. 3 is a diagram schematically illustrating signal division units according to various embodiments of the present invention.

FIG. 3 is a diagram schematically illustrating signal division unit 200 according to various embodiments of the present invention. Referring to FIGS. 1 and 3, according to an embodiment of the present invention, the signal s output from the pressure sensor unit 100 is divided into a DC signal z', which is output from the pressure sensor unit 100 when the pressure sensor unit 100 senses the atmospheric pressure Patm and the applied pressure Ppress, and an AC signal y', which is output from the pressure sensor unit 100 when the pressure sensor unit 100 senses the pressure Pskin delivered to the skin 101, through the signal division unit 200. The DC signal z' output from the pressure sensor unit 100 when the pressure sensor unit 100 senses the atmospheric pressure Patm and the applied pressure Ppress is generated through overlapping of a value according to the atmospheric pressure Patm and a value according to the applied pressure Ppress. The applied pressure Ppress is calculated by subtracting the atmospheric pressure Patm from a total pressure. In one embodiment, the signal division unit 200 may include a high-pass filter (HPF) unit 220 that separates only the AC signal y' from the electrical signal s output from the pressure sensor unit 100, and a low-pass filter (LPF) unit 240 that separates only the DC signal z' from the electrical signal s output from the pressure sensor unit 100. In another embodiment, the signal division unit 200 includes only the HPF unit 220 that separates only the AC signal y' from the electrical signal s output from the pressure sensor unit 100 as illustrated in FIG. 3(b), since the intensity of the AC signal y' is less than that of the DC signal z' in the electrical signal s output from the pressure sensor unit 100. In one embodiment, the HPF unit 220 or the LPF unit 240 may be embodied as at least one among a first-order filter, a second-order filter, and a higher-order filter. In another embodiment, the HPF unit 220 may be embodied as a capacitor 220' that blocks direct current as illustrated in FIG. 3(c).

Referring back to FIG. 1, the signal processor unit 300 processes the electrical signal. In one embodiment, the signal processor unit 300 includes an amplifier 320a that amplifies the input AC signal y', an analog-to-digital converter (ADC) 340a that converts the amplified AC signal y' into a digital signal, an amplifier/level shifter 320b that amplifies the DC signal z' to a level sufficient to convert the DC signal z' into a digital signal or that shifts a level of the DC signal z', and an ADC 340b that converts an output signal into a digital signal. In one embodiment, a signal s output from the signal division unit 200 may be the DC signal z' and the AC signal y', or a signal obtained by overlapping the DC signal z' and the AC signal y'. These signals may be directly converted into digital signals, but the AC signal y' has a far narrower swing width than the DC signal z' and thus is difficult to be converted into a digital signal having a maximum resolution. Thus, the AC signal y' is amplified by the amplifier 320a having a gain appropriate to be used as the maximum resolution. A digital signal y having a high resolution may be formed by inputting the amplified AC signal y' to the ADC 340a. Also, the amplifier/level shifter 320b converts the DC signal z' input to the signal processor unit 300 to a level appropriate to convert the DC signal z' into a digital signal, and inputs the converted DC signal z' to the ADC 340b. The converted DC signal z' is converted into a digital signal z by the ADC 340b. Although an arithmetic operation may be described below in a manner similar to a manner in which it is performed on an analog signal, the arithmetic operation is performed on a digital signal.

Figure 4:
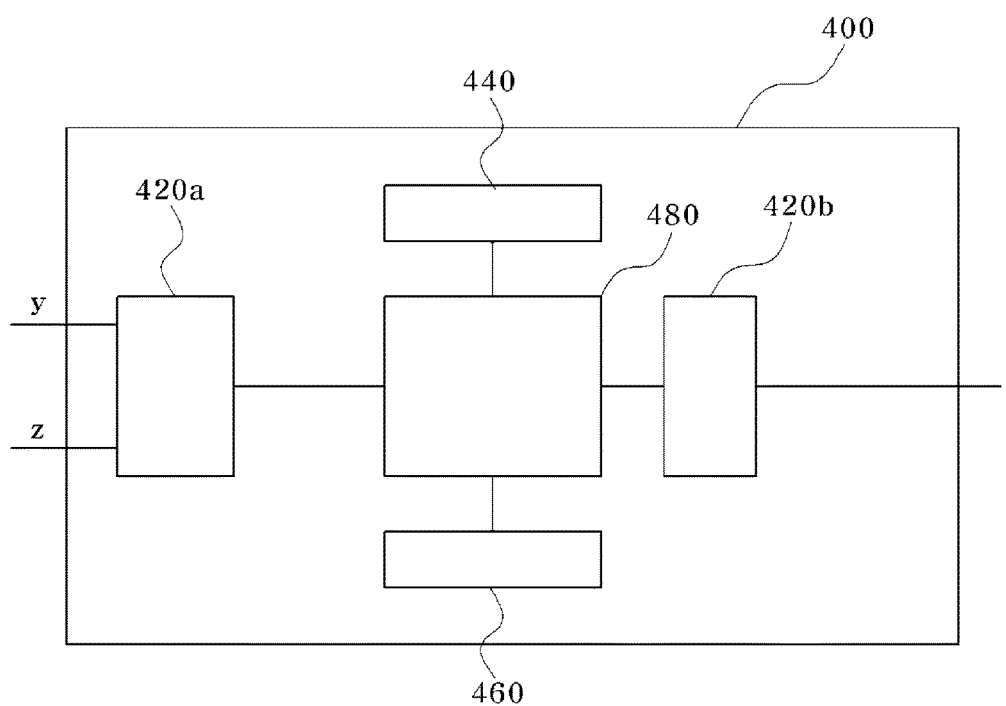
FIG. 4 is a schematic block diagram of a blood pressure calculation unit according to one embodiment of the present invention.
Figure 5:
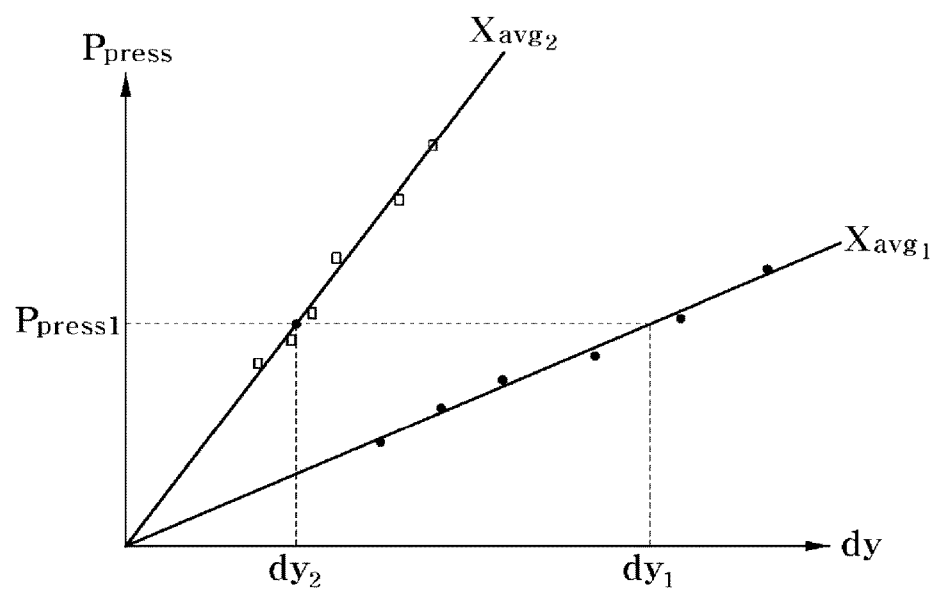
FIG. 5 is a graph illustrating a blood pressure average calculation method according to one embodiment of the present invention.

FIG. 4 is a schematic block diagram of the blood pressure calculation unit 400 according to one embodiment of the present invention. FIG. 5 is a graph illustrating a blood pressure average calculation method according to one embodiment of the present invention. A structure of the blood pressure calculation unit 400 and an operation of the blood pressure calculation unit 400 for calculating a blood pressure average will now be described with reference to FIGS. 1, 4, and 5. The blood pressure calculation unit 400 receives electrical signals y and z that are digitized by the signal processor unit 300, calculates an applied pressure Ppress, and calculates a blood pressure average based on the applied pressure Ppress and swing values of the electrical signals y and z. In one embodiment, the blood pressure calculation unit 400 includes an input/output (I/O) unit 420 including an input sub-unit 420a to which the electrical signals y and z that are processed by the signal processor unit 300 are input and an output sub-unit 420b that outputs the calculated blood pressure average; an arithmetic unit 440 that calculates the blood pressure average based on a signal converted into a digital signal by the signal processor unit 300; a memory unit 460 that stores input values and an arithmetic result value; and a control unit 480 that controls the I/O unit 420, the arithmetic unit 440, and the memory unit 460. In one embodiment, the blood pressure calculation unit 400 is embodied as one microcontroller unit (MCU) chip. In another embodiment, at least one among the arithmetic unit 440, the memory unit 460, the I/O unit 420, and the control unit 480 is embodied as a separate chip. In one embodiment, the arithmetic unit 440 calculates a blood pressure, etc. according to an algorithm implemented in hardware. In another embodiment, the arithmetic unit 440 calculates a blood pressure, etc. according to an algorithm implemented in software. Operations which will be described below using blood pressure calculation units according to embodiments of the present invention are intended to help understand the concept of the present invention but are not intended to limit the scope of the invention by the embodiments set forth herein. Thus, those of ordinary skill in the art could accomplish the present invention in different forms based on the concept of the present invention and thus the scope of the present invention should be understood as covering equivalents falling within the inventive concept disclosed herein.

In one embodiment, the input sub-unit 420a of the I/O unit 420 receives a pressure signal y that was delivered to the skin of a subject and converted into a digital signal, and a signal z which is a sum of the atmospheric pressure Patm and the applied pressure Ppress. The control unit 480 outputs the signals y and z to the arithmetic unit 440. The arithmetic unit 440 calculates the applied pressure Ppress from the signal z which is a sum of the atmospheric pressure Patm and the applied pressure Ppress. That is, if a pressure value of the DC signal z input to the I/O unit 420 is P, P=Patm+Ppress. Thus, the applied pressure Ppress may be calculated by subtracting the atmospheric pressure Patm from the input pressure value P.

Also, the signal y obtained by sensing pressure delivered to the skin of a subject has a maximum value and a minimum value according to a variation in a blood pressure in a blood vessel. The arithmetic unit 440 calculates a swing value dy that is the difference between the maximum and minimum values of the signal y obtained by sensing pressure delivered to the skin in each of predetermined periods, e.g., between systolic periods or between diastolic periods, and forms coordinate pairs indicated by "o" and "■" in FIG. 5, based on the swing value dy and the applied pressure Ppress in each of the periods. The control unit 480 stores the coordinate pairs in the memory unit 460, and the arithmetic unit 440 obtains straight lines Xavg1 and Xavg2 from the stored coordinate pairs according to an averaging algorithm such as a recursive averaging algorithm or the like. In the case of the straight line Xavg1 of FIG. 5, the lower the applied pressure Ppress, the less the swing value dy of the signal y obtained by sensing the pressure delivered to the skin, and the higher the applied pressure Ppress, the greater the swing value dy. That is, when the pressure delivered to the skin is measured while increasing pressure applied onto a blood pressure meter, blood vessels and subcutaneous tissues are pressed to increase the rate of transfer of pressure via the subcutaneous tissues, thereby increasing a swing width dy of the pressure applied to the skin.

The inventor of the present invention found that the slope of a straight line formed by the swing value dy in a specific time period and the applied pressure Ppress is proportional to a blood pressure average of a subject, and the blood pressure average may be calculated from the slope of the straight line. That is, a blood pressure average of a subject corresponding to a line with a steep slope such as the straight line Xavg2 is higher than that of a subject corresponding to a line with a slight slope such as the straight line Xavg1. According to the inventor of the present invention, the relation between the slope of a line measured as described above and a blood pressure average is expressed by Equation 1 below.

$$X_{avg} = \frac{(\text{slope} + 0.1173)}{0.001933} \quad [\text{Equation 1}]$$

$X_{avg}$: blood pressure average, slope: slope of straight line

Thus, the arithmetic unit 440 forms a straight line by performing an arithmetic operation on the coordinate pairs stored in the memory unit 460 according to an averaging algorithm such as the recursive averaging algorithm. Since the blood pressure of a human being and an applied pressure are finite values, the coordinate pairs have finite values and thus the slope of the straight line converges to a finite value even when an averaging algorithm such as the recursive averaging algorithm is performed. The recursive averaging algorithm is one example of an averaging algorithm available in one embodiment of the present invention. Thus, the present invention is not limited thereto and a straight line may be formed using various averaging algorithms. The arithmetic unit 440 may calculate a slope value of the formed straight line, and calculate the blood pressure average of the subject based on Equation 1 above using the slope value. In one embodiment, the control unit 480 stores a blood pressure average measured by the arithmetic unit 440 in the memory unit 460. In one embodiment, the control unit 480 transmits a blood pressure average calculated by the arithmetic unit 440 to the output sub-unit 420b of the I/O unit 420.

A method of calculating a blood pressure average will be described below. The signal y obtained by sensing the pressure delivered to the skin is expressed by Equation 2 below.

$$y = x \times A \times S \times G + y0 \quad [\text{Equation 2}]$$

x: pressure of blood pressure,
A: rate of transfer of pressure of subcutaneous tissue
S: sensitivity of pressure of sensor, G: gain of amplifier y0: offset values of sensor and amplifier Thus, the swing value dy of the signal y obtained by sensing the pressure applied to the skin is expressed by Equation 3 below.

$$dy = dx \times A \times S \times G \quad \text{[Equation 3]}$$

In Equation 3, the swing value dy is proportional to a pulse pressure dx, that is the difference dx between a systolic pressure which is a maximum blood pressure and a diastolic pressure which is a minimum pressure, and is calculated by the product of the pulse pressure dx, the rate A of transfer of pressure via a subcutaneous tissue, the sensitivity S of a sensor to pressure, and the gain G of an amplifier. In general, it is medically known that the higher the blood pressure average of a person, the higher the pulse pressure dx. Thus, when an applied pressure Ppress1 is the same, the higher the blood pressure average, the greater the swing value dy should be. However, an experiment result revealed that when the same applied pressure Ppress was applied to the subject corresponding to the straight line Xavg2 of a high average blood pressure and the subject corresponding to the straight line Xavg1 of a low average blood pressure, a swing value dy1 of the straight line Xavg1 was greater than a swing value dy2 of the straight line Xavg2. This is because the rate A of transfer of pressure of a subject having a relatively high blood pressure via a blood vessel and subcutaneous tissue is lower than the rate of transfer of pressure of the subject having a relatively low blood pressure. Thus, in the case of the straight line Xavg1, even if the same applied pressure Ppress is applied, the swing value dy was large. Thus, with the pressure sensor unit 100 that senses a pressure at a constant sensitivity S and the signal processor unit 300 that processes an electrical signal with a constant gain G, a blood pressure average Xavg and the rate of transfer of pressure via subcutaneous tissue may be measured through an arithmetic calculation using a swing value dy of an electrical signal obtained by sensing pressure delivered to the skin of a subject and an applied pressure.

Figure 6:
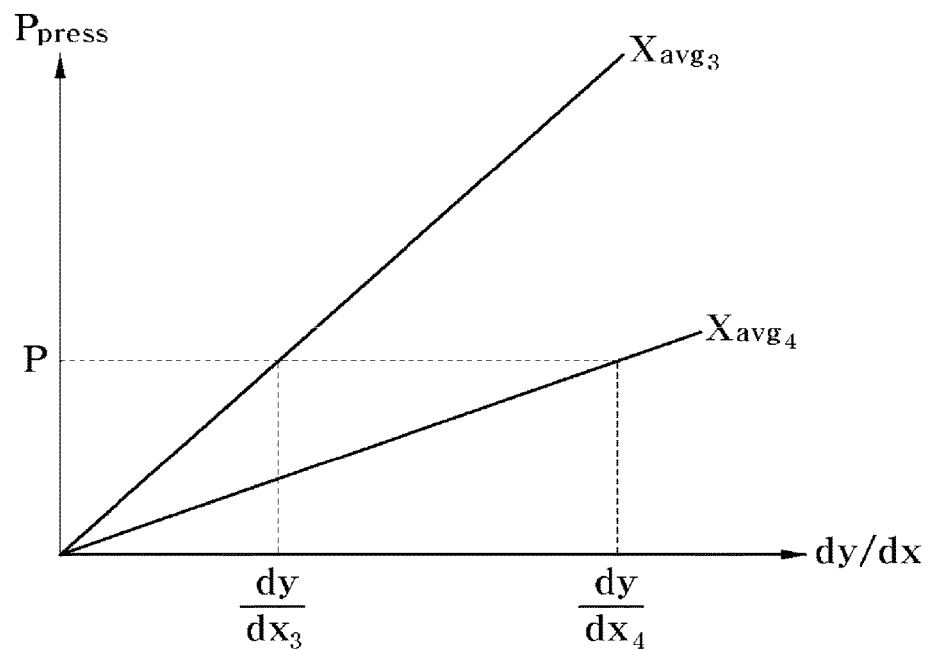
FIG. 6 is a graph illustrating a pulse pressure calculation method according to one embodiment of the present invention.

FIG. 6 is a graph illustrating a pulse pressure calculation method according to one embodiment of the present invention. An operation of the blood pressure calculation unit 400 for calculating a pulse pressure dx will now be described with reference to FIGS. 1, 4, and 6. The blood pressure calculation unit 400 calculates a blood pressure average by performing the operation described above. The inventor of the present invention found that a relation between a value dy/dx, which is obtained by dividing a swing value dy of an electrical signal obtained by sensing applied pressure Ppress and pressure Pskin delivered to the skin of a subject, by a pulse pressure dx, which swings between a systolic pressure which is a maximum blood pressure and a diastolic pressure which is a minimum blood pressure, and the applied pressure Ppress is expressed in the form of a straight line as illustrated in FIG. 6. The relation between the value dy/dx and the applied pressure Ppress is expressed by Equation 4 below.

$$P_{press} = a \times \frac{dy}{dx} \quad \text{[Equation 4]}$$

In Equation 4, a slope a is relevant to the blood pressure average. The relation between the slope a and the blood pressure average is expressed by Equation 5 below.

$a = 0.07811 \times (Xavg) - 4.449$  $X_{avg}$: blood pressure average  [Equation 5]

Thus, the pulse pressure dx may be calculated in conjunction with Equations 4 and 5, as shown in Equation 6 below.

$$dx = dy \times \frac{0.07811 \times X_{avg} - 4.449}{P_{press}} \quad \text{[Equation 6]}$$

Thus, the pulse pressure dx may be calculated by calculating Equation 6 using the swing value dy, the applied pressure Ppress, and the blood pressure average Xavg stored in the memory unit 460 during the calculation of a blood pressure average. Accordingly, a maximum blood pressure Xmax which is a systolic pressure may be calculated by adding half the pulse pressure dx to the blood pressure average Xavg, and a minimum blood pressure Xmin which is a diastolic pressure may be calculated by subtracting half the pulse pressure dx from the blood pressure average Xavg. To perform the arithmetic operation, the control unit 480 transmits to the arithmetic unit 440 information regarding the blood pressure average Xavg and information regarding a coordinate pair of the swing value dy and the applied pressure Ppress stored in the memory unit 460. The arithmetic unit 440 calculates Equation 6 based on the transmitted information, and stores the calculated pulse pressure dx, the maximum blood pressure Xmax, the minimum blood pressure Xmin, etc. in the memory unit 460. Also, the control unit 480 transmits the calculated average blood pressure, the pulse pressure dx, the maximum blood pressure Xmax, the minimum blood pressure Xmin to the output sub-unit 420*b* of the I/O unit 420 to transmits these values to the outside or to display them on a blood pressure display unit.

Referring to FIG. 1, in one embodiment, the communication unit 500 transmits a blood pressure average, a pulse pressure, a maximum/minimum blood pressures, etc., which are received from the I/O unit 420, to at least one among an external server (not shown), a terminal (not shown), and a display device (not shown) of the pressure sensor unit 100 by communicating the at least one through at least one of wired communication and wireless communication. In one embodiment, the communication unit 500 may communicate with the external server or the terminal using at least one communication protocol among Wifi, Bluetooth, ZigBee, infrared (IR) communication. However, the present invention is not limited thereto. In another embodiment, the communication unit 500 may communicate with a server outside a blood pressure measuring apparatus through wireless/wired communication to transmit the blood pressure average, the pulse pressure, etc. to the server. Thus, the server may continuously monitor a blood pressure state of a subject by communicating with a blood pressure measuring apparatus according to an embodiment of the present invention. In another embodiment, the communication unit 500 may transmit the blood pressure average, the pulse pressure, etc. to an external terminal by communicating with the external terminal through wireless/wired communication. In one embodiment, a terminal may be one of a mobile phone, a smartphone, a personal digital assistant (PDA), and a tablet personal computer (PC) capable of communicating with a blood pressure measuring apparatus according to an embodiment of the present invention. In another embodiment, the communication unit 500 transmits blood pressures, such as a calculated average blood pressure, a maximum blood pressure, a minimum blood pressure, etc. to a display unit (not shown) of the pressure sensor unit 100 to display the blood pressures on the display unit. In one embodiment, the display unit may be a liquid crystal display (LCD) device formed on a surface of the pressure sensor unit 100 and capable of displaying the measured blood pressure thereon. Thus, a subject is able to conveniently monitor his/her blood pressure state via a terminal at any time and thus prevent an accident from occurring due to an increase or a decrease in his/her blood pressure.

Figure 7:
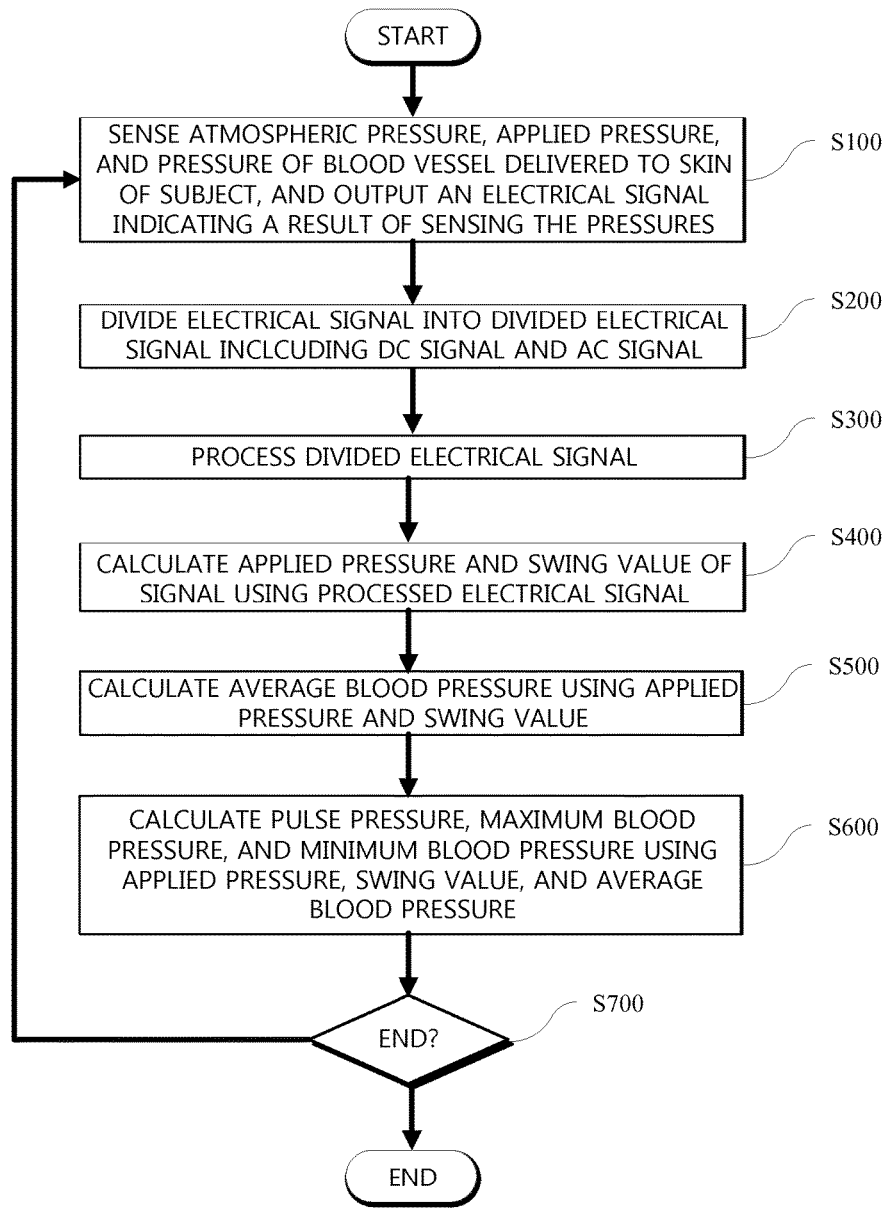
FIG. 7 is a brief flowchart of a blood pressure measuring method according to one embodiment of the present invention.

A blood pressure measuring method according to an embodiment of the present invention will be described with reference to the accompanying drawings below. Overlapping portions between the blood pressure measuring method and the above blood pressure measuring apparatus are omitted here for convenience of explanation. FIG. 7 is a brief flowchart of a blood pressure measuring method according to one embodiment of the present invention. Referring to FIG. 7, a pressure sensor unit is placed on a portion of a subject, the blood pressure of whom is to be measured, to sense atmospheric pressure Patm, applied pressure Ppress, and the pressure of a blood vessel delivered to the skin of the subject and to output an electrical signal indicating a result of sensing the pressures (S100). An electrical signal output by sensing the atmospheric pressure Patm and the applied pressure Ppress is in the form of a DC signal, a variation in the intensity of which is zero or small according to time, and an electrical signal output by sensing the pressure in the blood vessel delivered to the skin is in the form of an AC signal.

The output electrical signal is divided into a DC signal and an AC signal (S200). In one embodiment, the electrical signal output by sensing the atmospheric pressure Patm, the applied pressure Ppress, and the pressure of the blood vessel delivered to the skin is a signal obtained by overlapping the DC signal and the AC signal. Thus, only the AC signal may be obtained by filtering the electrical signal using a high-pass filter or a capacitor. In another embodiment, only the DC signal may be obtained by filtering the electrical signal using a low-pass filter. In another embodiment, an AC signal may be obtained using a high-pass filter or a capacitor, and a signal obtained by overlapping a DC component with an AC component may be used, since the magnitude of an AC component is lower than that of a DC component in the electrical signal output from the pressure sensor unit.

Next, the DC signal and the AC signal are processed (S300). In one embodiment, the processing of the DC signal and the AC signal (S300) includes a process of amplifying the magnitude of the AC signal to correspond to the resolution of an ADC and a process of converting the amplified AC signal into a digital signal having a constant resolution. In one embodiment, the processing of the DC signal and the AC signal (S300) includes a process of amplifying the DC signal or shifting the level of the DC signal, and converting the resultant DC signal into a digital signal. In one embodiment, a signal converted into a digital signal has a resolution having 256 levels ranging from 0 to 255 when data obtained through the ADC is 8 bits long, and has a resolution having 1024 levels ranging from 0 to 1023 when data obtained through the ADC is 10 bits long.

Next, the applied pressure Ppress and a swing value of the AC signal are calculated using the processed DC and AC signals (S400). In one embodiment, the pressure sensor unit senses a pressure which is the sum of the atmospheric pressure Patm and the applied pressure Ppress, and the applied pressure Ppress is calculated by subtracting the atmospheric pressure Patm from the sensed pressure. In one embodiment, a swing value dy of the electrical signal is calculated. As described above, the processed electrical signal swings due to a variation in the pressure applied to the skin rather than a variation in the atmospheric pressure Patm or the applied pressure Ppress. In one embodiment, the calculated applied pressure and swing value are stored in a memory in the form of a coordinate pair.

A blood pressure average Xavg is calculated using the applied pressure Ppress and the swing value dy of the processed electrical signal (S500). As described above, a slope of a straight line formed by coordinate pairs of the swing value dy and the applied pressure Ppress in target time periods is proportional to a blood pressure average of the subject, and the blood pressure average may be measured from the slope of the straight line. That is, a blood pressure average is lower when a straight line with a slight slope is formed by coordinate pairs of the swing value dy and the applied pressure Ppress in the target time periods than when a straight line with a steep slope is formed by coordinate pairs of the swing value dy and the applied pressure Ppress in the target time periods. The relation between the slope of such a straight line and a blood pressure average is shown in Equation 1 above. Thus, a blood pressure average of the subject may be calculated by calculating the slope of the straight line formed by coordinate pairs of the swing value dy and the applied pressure Ppress and calculating Equation 1 based on the calculated slope.

A pulse pressure dx, a maximum blood pressure Xmax, and a minimum blood pressure Xmin are calculated using the blood pressure average Xavg, the swing value dy, and the slope (S600). As described above, the relation between a value dy/dx obtained by dividing the swing value dy by the pulse pressure dx and the applied pressure Ppress may be expressed in the form of a straight line as illustrated in FIG. 6, and the pulse pressure dx may be expressed as Equation 6 above, based on Equations 4 and 5. Thus, the pulse pressure dx may be calculated by calculating Equation 6 using the swing value dy, the applied pressure Ppress, and the blood pressure average Xavg which are stored in the memory unit 460 during the calculation of the blood pressure average Xavg, the maximum blood pressure Xmax may be calculated by adding half the pulse pressure dx to the blood pressure average Xavg, and the minimum blood pressure Xmin may be calculated by subtracting half the pulse pressure dx from the blood pressure average Xavg. Next, whether the blood pressure is to be measured or not is determined (S700), and the blood pressure is continuously measured or measurement of the blood pressure is ended.

In one embodiment, the calculated blood pressures such as the blood pressure average Xavg, pulse pressure dx, the maximum blood pressure Xmax, and the minimum blood pressure Xmin are transmitted to an external server through wired/wireless communication. The blood pressure of the subject may be monitored at any time at a location distant from the subject, based on the calculated blood pressures transmitted to the external server. In another embodiment, the calculated blood pressures such as the blood pressure average Xavg, the pulse pressure dx, the maximum blood pressure Xmax, and the minimum blood pressure Xmin are transmitted to a terminal through wired/wireless communication. Based on the calculated blood pressures transmitted to the terminal, the subject is able to conveniently measure his/her blood pressure at any time, thereby preventing in advance an accident from occurring, due to a sharp change in his/her blood pressure.

With a blood pressure measuring apparatus and method according to the present invention, a blood pressure average, a pulse pressure, a maximum blood pressure, and a minimum blood pressure can be calculated by measuring a variation in a swing value dy in a situation in which an applied pressure Ppress changes. Also, the precision of measuring a blood pressure can be improved through continuous data sampling.

The present invention has been particularly shown and described with reference to the embodiments illustrated in the appended drawings. The embodiments are, however, provided as examples only used for a better understanding of the present invention. It would be obvious to those of ordinary skill in the art that the above embodiments are to cover all modifications, equivalents, and alternatives falling within the scope of the invention. Accordingly, it will be understood that various changes in form and details may be made therein without departing from the spirit and scope of the following claims.

The invention claimed is:

1. An apparatus for measuring blood pressure, the apparatus comprising:
a pressure sensor unit configured to sense a static pressure, which is the sum of an atmospheric pressure and an applied pressure, and a blood pressure of a blood vessel delivered to a subject body, and output an electrical signal based on the sensed static pressure and the sensed blood pressure, while in contact with the subject body;
a signal division circuitry configured to receive the electrical signal and divide the electrical signal into a direct current (DC) signal component and an alternating current (AC) signal component;
a signal processor configured to process the DC signal component and the AC signal component;
a blood pressure calculation circuitry configured to calculate the applied pressure using the processed DC signal component and calculate a blood pressure average using calculated applied pressures and swing values of the processed AC component; and
a display configured to display blood pressure values calculated by the blood pressure calculation circuitry,
wherein a swing value of the processed AC signal component is a difference between the maximum and minimum values of the processed AC signal component, and
wherein the blood pressure calculation circuitry is embedded in a microprocessor chip and configured to calculate the blood pressure average using a slope of a line being formed by a plurality of coordinate pairs of the calculated applied pressures and the swing values of the processed AC signal component.

2. The apparatus of claim 1, wherein the pressure sensor unit comprises:
a housing including a concave portion which forms an airtight space inside the concave portion; and
a pressure sensor installed in the housing and configured to sense a pressure of air trapped in the airtight space formed by the concave portion while a portion, of the housing, surrounding the concave portion is in contact with the subject body.

3. The apparatus of claim 1, wherein the pressure sensor unit senses the atmospheric pressure and the applied pressure together, senses the pressure of the blood vessel delivered to the subject body, and outputs the electric signal including the DC signal component indicating a result of sensing the atmospheric pressure and the applied pressure together, and the AC signal component indicating a result of sensing the delivered pressure.

4. The apparatus of claim 1, wherein the signal processor comprises:
an amplifier configured to amplify an input signal; and
an analog-to-digital converter (ADC) configured to perform digital conversion on the amplified input signal.

5. The apparatus of claim 1, wherein the signal processor comprises:
an amplifier configured to amplify an input signal;
a level shifting circuitry configured to shift a level of the input signal; and
a plurality of analog-to-digital converters (ADCs) configured to perform digital conversion on outputs of the amplifier and the level shifting circuitry.

6. The apparatus of claim 1, wherein the signal division circuitry comprises a high-pass filter unit configured to remove the DC signal component from the electrical signal output from the pressure sensor unit while outputting the AC signal component.

7. The apparatus of claim 6, wherein the high-pass filter unit comprises at least one of a first or higher order high-pass filter and a capacitor.

8. The apparatus of claim 1, wherein the blood pressure calculation circuitry comprises:
an arithmetic unit configured to calculate the blood pressure average by performing an arithmetic operation on the calculated applied pressures and the swing values of the processed AC signal component;
a memory unit configured to store the calculated applied pressures and the swing values of the processed AC signal component;
an input/output (I/O) unit configured to receive a signal from the signal processor and output a value calculated by the arithmetic unit; and
a control unit configured to control the arithmetic unit, the memory unit, and the I/O unit.

9. The apparatus of claim 1, further comprising a communication unit configured to communicate with at least one of an external server and a terminal through wired/wireless communication to transmit the blood pressure values calculated by the blood pressure calculation circuitry to at least one of the external server and the terminal.

10. The apparatus of claim 1, wherein the blood pressure calculation circuitry is configured to calculate the applied pressure by subtracting the atmospheric pressure from the static pressure sensed by and output from the pressure sensor unit.

11. The apparatus of claim 10, wherein the blood pressure calculation circuitry is configured to calculate a rate of transfer of pressure via subcutaneous tissue, based on the applied pressure.

12. The apparatus of claim 1, wherein the blood pressure calculation circuitry is configured to calculate a pulse pressure by dividing a value, which is obtained by subtracting a second constant from the product of the blood pressure average and a first constant, by the applied pressure.

13. The apparatus of claim 1, wherein the blood pressure average is calculated from the following formula:

$$X_{avg} = \frac{(slope + 0.1173)}{0.001933},$$

wherein the $X_{avg}$ is the blood pressure average, and the slope is the slope of the line.

* * * * *